United States Patent
Richart et al.

(12) 
(10) Patent No.: US 6,316,091 B1
(45) Date of Patent: *Nov. 13, 2001

(54) METHOD FOR PREPARING SYNTHETIC BONE SUBSTITUTES WITH CONTROLLED POROSITY

(75) Inventors: Olivier Richart, Deggendorf; Stephan Szarzynski, Haulchin; Pierre Hardouin, Le Touquet; Michel Descamps, Wallers; Amparo Gallur-Greme, Toulouse, all of (FR)

(73) Assignee: SDGI Holdings, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,017
(22) PCT Filed: Feb. 5, 1998
(86) PCT No.: PCT/FR98/00213
  § 371 Date: Nov. 18, 1999
  § 102(e) Date: Nov. 18, 1999
(87) PCT Pub. No.: WO98/34654
  PCT Pub. Date: Aug. 13, 1998

(30) Foreign Application Priority Data

Feb. 5, 1997 (FR) .................................................. 97 01309

(51) Int. Cl.[7] .......................... A61L 27/00; C04B 35/447
(52) U.S. Cl. ........................... 428/310.5; 264/43; 264/44; 264/321; 264/327; 264/333; 264/337; 428/312.2; 501/81; 623/923; 623/926
(58) Field of Search .............................. 428/310.5, 312.2; 264/43, 44, 321, 327, 333, 337; 501/81; 623/923, 926

(56) References Cited

U.S. PATENT DOCUMENTS

| | | | | |
|---|---|---|---|---|
| 4,371,484 | * | 2/1983 | Inukai et al. | 264/44 |
| 5,298,205 | * | 3/1994 | Hayes et al. | 264/414 |
| 5,958,314 | | 9/1999 | Draenert | 264/42 |

FOREIGN PATENT DOCUMENTS

| | | |
|---|---|---|
| 31 23 460 A1 | 2/1982 | (DE) . |
| 4403 509 | 8/1995 | (DE) . |
| WO92/0665A1 | 4/1992 | (WO) . |
| WO95/32008 | 11/1995 | (WO) . |

* cited by examiner

*Primary Examiner*—Blaine Copenheaver
*Assistant Examiner*—Leanna Roche
(74) *Attorney, Agent, or Firm*—Woodard, Emhardt, Naughton, Moriarty & McNett

(57) ABSTRACT

The invention concerns a method for preparing macro-porous synthetic ceramics designed in particular for bone substitution. The invention also concerns macro-porous synthetic ceramics comprising pores of controlled dimensions, distributed in number and in surface in a predetermined manner, the interconnection between the pores thereof being controlled.

16 Claims, 5 Drawing Sheets

METHOD FOR PREPARING SYNTHETIC BONE SUBSTITUTES WITH CONTROLLED POROSITY

BACKGROUND OF THE INVENTION

The invention relates to a process for preparing a macroporous synthetic ceramic intended especially as a bone replacement, the ceramic having a controlled interconnection dimension between the pores, as well as a controlled porosity and a controlled pore size.

The processes of the aforementioned type, known from the prior art, have a number of drawbacks.

This is because these processes do not allow the porous architecture of the ceramic obtained to be completely controlled, namely especially to control not only the size and shape of the macropores and their distribution within the ceramic matrix but also the size of the interconnections between macropores.

Now, this lack of control reduces the biological effectiveness of the ceramics, which is characterized, in the case of an application as a bone replacement, by poor bone rehabilitation or, at the very least, partial rehabilitation of the bone replacement.

In addition, heterogeneities in the mechanical behaviour, especially in compression, are often found because of the imperfect reproducibility of the architectures.

Certain processes recommend exerting pressure on the compacted particles intended to form the pores, so as to control the interconnection diameter.

However, this type of process does not allow effective control of the interconnection, which is homogeneous, easily reproducible and modifiable.

Moreover, the structural heterogeneities in the ceramic bone replacements of the prior art often cause variations in the mechanical behaviour.

Because the architectures are not completely controlled, the mechanical strength is often low, particularly in compression. It is necessary to limit the mechanical stresses on the implant and, consequently, to reduce the size of the manufactured components for the purpose of limiting the risk of mechanical failure of the implant/receiving bone system.

The prior art is represented, in particular, by documents WO-A-92/06653, DE-A-4,403,509, DE-A-3,123,460 and WO-A-95/32008.

SUMMARY OF THE INVENTION

The object of the invention is therefore to alleviate the drawbacks of the aforementioned prior art.

Thus, one objective of the process of the invention is especially:

- to control the interconnection between the macropores of a synthetic ceramic in a reproducible and modifiable manner so as, in particular, to allow the passage of bone cells and thus to ensure bone neoformation right into the core of the biomaterial in the case of an application as a bone replacement, this control of the interconnection having to be implemented in a homogeneous manner and right into the core of the replacement, whatever its size;
- to control the porosity of the ceramic and the dimensions of the pores;
- to produce biocompatible ceramics, "on request", having dimensions and a predefined shape.

For this purpose the invention proposes a process of the aforementioned type, characterized by the following successive steps:

a) construction of an edifice from pore-forming elements;
b) thermoforming of the edifice so as to ensure controlled coalescence between the pore-forming elements;
c) impregnation of the edifice with a suspension so as to fill the spaces between the pore-forming elements;
d) removal of the pore-forming elements so as to generate the macroporosity with a controlled interconnection diameter.

More specifically, according to the process of the invention, particles of a pore-forming organic compound of low thermal expansion are packed into a container, the particles having a predetermined shape.

In order for there to be intimate contact between the particles, and therefore for the interconnection between macropores to be generated, the particles are subjected to a thermoforming treatment.

The purpose of this operation is to reach the working temperature, greater than the glass transition temperature of the organic compound, so as to place it in its rubbery plateau, so as to produce controlled welding between these particles.

The generation of the controlled bridging between particles, and therefore of the future controlled interconnection between macropores, is achieved by regulating the thermoforming treatment time parameter and the thermoforming treatment temperature parameter.

Other approaches are possible if it is desired to reduce the treatment time. It is possible, for example, to increase the working temperature (without however reaching the decomposition temperature of the polymer) or else to apply pressure to the polymeric edifice (at a temperature above the glass temperature) so as to speed up the development of the welds which form.

Once the connections have been made between the particles, the monobloc formed by these interconnected particles is extracted, after the structure has cooled, in order to place it in a porous mold.

The spaces between the particles are then filled up with a calcium phosphate powder in suspension in an aqueous medium so as to form the ceramic reinforcement of the material.

After removing the water via the porous structure of the mold, the product obtained is demoulded and then heat-treated so as, in a first step, to remove the organic compound, and therefore to generate the porosity of the product, and then, in a second step, to densify the walls of the ceramic.

According to the invention, the organic compound is chosen especially from acrylic resins, such as, in particular, polymethyl methacrylate (PMMA) and polymethacrylate (PMA), polystyrene, polyethylene or similar materials.

Furthermore, in one embodiment of the invention, the particles have an approximately spherical general shape.

According to the invention, the calcium phosphate is chosen especially from hydroxyapatite (HA) or tricalcium phosphate ($\beta$ TCP), or the like, or a mixture of them.

The process of the invention thus makes it possible to obtain a macroporous synthetic ceramic whose interconnection between macropores is perfectly controlled and whose pores have controlled dimensions and are distributed, in terms of number and area, in a predetermined manner.

More specifically, the process of the invention allows perfect control of the diameter of the spherical pores, especially between 100 $\mu$m and 800 $\mu$m, with perfectly controlled interconnections, especially between 0.1 and 0.8 times the diameter of the macropore involved, and more particularly between 40 and 640 $\mu$m.

Moreover, control of the parameters, such as the treatment temperature, the treatment pressure and the treatment time, allows the interconnection diameter to be controlled.

A polymer redistribution law at a temperature above the glass transition temperature, of the viscous-flow type, for the formation of interparticle necks, governs the coalescence of the particles and thus allows the final interconnection diameter to be perfectly controlled.

For experimental implementation reasons, ceramics are produced in which the interconnection diameter between the macropores is greater than 30 μm. Consequently, for each given particle-size class of beads, the coalescence, and therefore the final interconnection of the product, can be precisely adjusted. It should be understood that these two parameters are distinct from each other and can be adjusted independently.

The invention also makes it possible to obtain ceramics of the aforementioned type in any size, whether these are small or large (several cm³), and having a high mechanical strength.

Furthermore, this process also makes it possible to obtain ceramics that can be bone replacements of complex shape and of constant or variable porosity.

Finally, according to another aspect, the invention relates to the use of such a ceramic as a bone replacement.

Other features and advantages of the invention will emerge from the description that follows, with reference to the appended drawings and illustrations.

Figure 1:
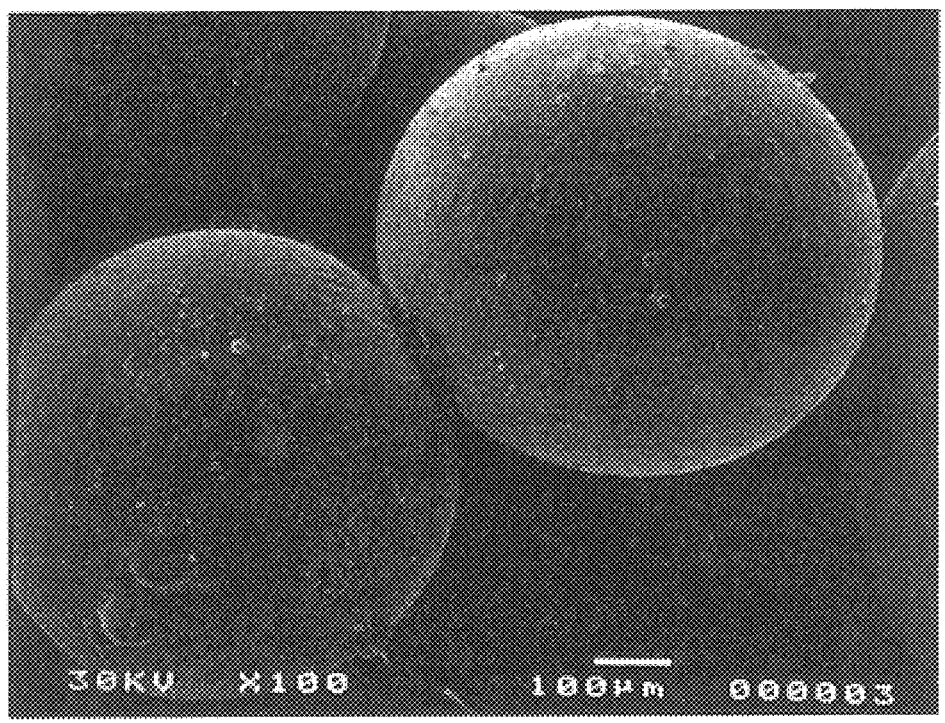
FIG. 1 is an electron microscope image showing the coalescence of polymer particles.

It is also conceivable to use polyethylene, polymethacrylate or polystyrene particles.

The common point between these compounds is especially their pore-forming property.

DETAILED DESCRIPTION

In general, any organic compound may be chosen that has a low thermal expansion in order to prevent deterioration of the compound during a thermal cycle.

A thermoplastic polymer, capable of being thermoformed, will consequently be chosen.

Moreover, in one particular embodiment, a polymer will be used that has an at least partially amorphous structure, preferably a completely amorphous structure, so as to avoid too great a volume increase during the heat treatment.

Finally, the pore-forming element must be able to degrade at low temperature with a negligible level of residual impurities and of non-corrosive decomposition products.

Typically, PMMA corresponds to a compound having all these properties.

Thus, in the rest of the description, reference will be made to PMMA particles, it being understood that any other compound having the aforementioned properties may be used.

The PMMA particles used are in the form of beads which may have dimensions which are approximately identical to each other or different diameters.

In the latter case, it is conceivable to place in the bottom of the container a certain number of small-sized balls on which larger-sized balls rest. Such an arrangement will make it possible to obtain a ceramic having different porosities.

It is also conceivable to arrange different layers of beads in the container, the diameter of the beads increasing as they are being packed. Thus, a ceramic with a porosity gradient is obtained.

The spherical shape of the PMMA particles makes it possible in particular to ensure that there are intimate and various contacts between the particles, to obtain a porosity of homogeneous morphology and to control the final pore volume of the ceramic.

This is because PMMA particles have the particular feature of being non-deformable or of deforming only slightly, as indicated above.

As a result, the pores of the replacement obtained have dimensions approximately the same as those of the particles.

The PMMA beads used have, in one particular embodiment, a particle size whose distribution extends from a few microns to approximately 850 microns.

In order to control the dimensions of the macropores of the ceramic obtained, the PMMA powder is subjected beforehand to a mechanical screening operation.

For the purpose, the PMA powder is passed between screens of different mesh openings, so as to obtain batches of powder of relatively narrow particle-size classes.

It is thus possible to select particle-size classes ranging from 0 to 100 μm, from 100 to 200 μm, from 200 to 300 μm, from 400 to 500 μm, from 500 to 600 μm, from 600 to 700 μm or from 700 to 850 μm.

It should be understood that narrower particle-size classes—from 190 to 200 μm for example—may be selected.

It should be noted that some of the PMMA beads may be hollow.

It should be understood that the number, the shape and the distribution of the particles used depends on the shape of the mold and on the ceramic that it is desired to obtain.

The container intended to receive the particles of organic compound must be able to withstand at least the thermal degradation temperature of the said compound.

In the present case in which an acrylic resin, and more particularly PMMA, is used, this temperature is about 200° C.

Thus, the container is, for example, metallic, ceramic or polymeric.

In a second step, the PMMA particles undergo a thermoforming treatment so as to ensure coalescence between the said particles.

In fact, an amorphous polymer, such as PMMA in particular, assumes a rubbery consistency at a temperature above the glass transition temperature $T_g$ of the said polymer.

It will be recalled that the glass transition temperature of PMMA is about 110° C.

Thus, at a temperature above the glass transition temperature, the polymer undergoes modifications of its macromolecules in order to achieve the rubbery consistency close to the viscous state. The polymer can therefore be easily modelled.

When the material is in this somewhat plastic state, contact between the particles allows, by diffusion mechanisms, at least partial interlocking of some of the macromolecules contained in the various particles, resulting in them being welded together.

Once the desired state has been obtained, it is fixed by simply returning to room temperature.

This is because the viscosity of the material obtained then gradually increases when the temperature decreases.

The thermoforming process consists, in general, in homogeneously heating the particles, as a whole or on their surface, at a temperature above the glass transition temperature of the organic compound.

The PMMA thermoforming treatment may be divided into the following steps:
preheating the empty container at a temperature above that of the glass transition of the PMMA, in this case above approximately 110° C.;
introducing the PMMA beads into the container;
forming and welding the beads until the end of cooling;
cooling to room temperature.

According to another embodiment, it is possible not to preheat the container when empty but to heat it when filled.

The technique of thermoforming these pore-forming elements is reproducible and also applicable to edifices of a large area (several tens of square centimeters) and of large volume (several tens of cubic centimeters).

The effectiveness of the procedure for controlling the interconnection diameter is essentially diffusion-controlled, the quality of the welds will depend on the temperature, the time and the intensity of the interparticle contact.

In order to determine the optimum temperature for forming the polymer, the PMMA beads are introduced into a metal container preheated, for example, to various treatment temperatures.

These temperatures, above the glass transition temperature, are 120° C., 150° C., 180° C. and 200° C., respectively.

These tests have made it possible to monitor the change in the bridging between beads as a function of the thermoforming time. This analysis is carried out by scanning electron microscopy.

These tests are carried out firstly on PMMA beads having a particle-size distribution of between 500 and 600 $\mu$m. For each manipulation, a constant weight of beads equal to 5 grams is introduced into a cylindrical container having a diameter of 26 millimeters.

For a treatment temperature of 120° C. and for heating times longer than 20 hours, there is no cohesion between the beads. This temperature seems to be insufficient to allow, in the times in question, diffusion and sufficient bridging between the polymer beads.

Figure 5:
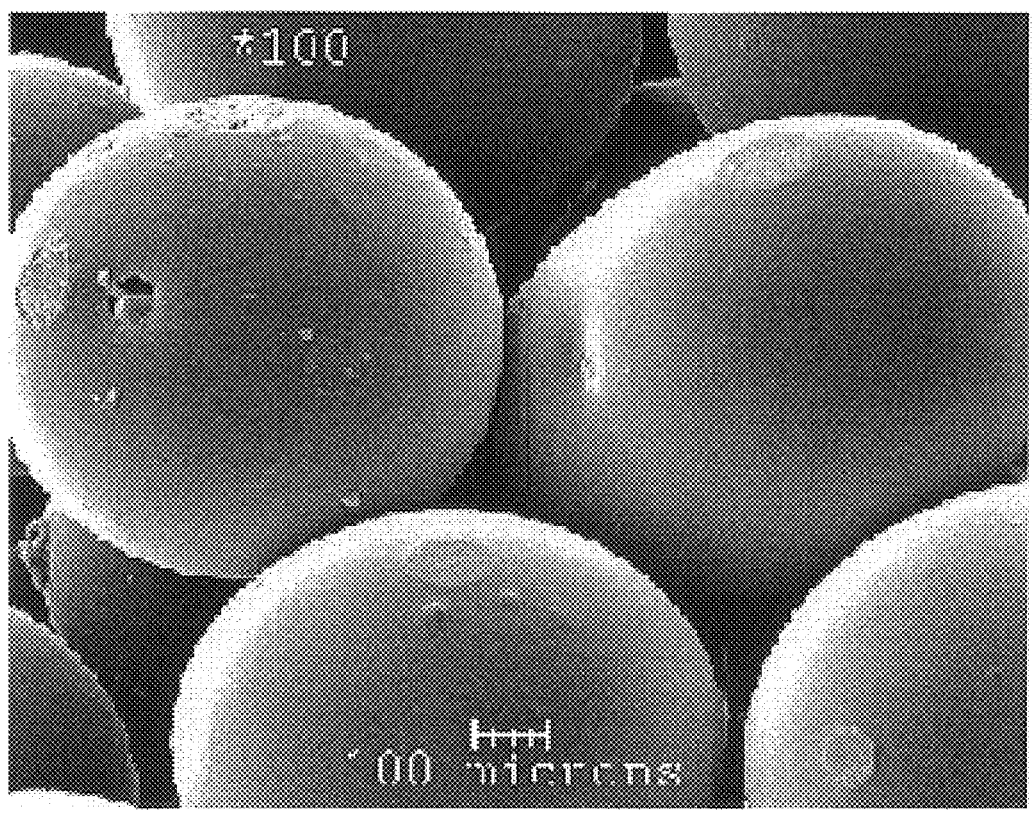
FIG. 5 is an electron microscope image of particles that have undergone a heat treatment at 150° C.

This interparticle cohesion becomes apparent at a temperature of 150° C. (see FIG. 5, in which particles of diameter between 500 and 600 $\mu$m have undergone a treatment at 150° C. for 16 hours).

However, long times are necessary in order for the PMMA particles to be welded together correctly. Scanning electron microscope analysis of specimens treated for 16 hours makes it possible to observe the contact area between the beads and therefore to evaluate the effectiveness of the thermoforming operation.

This contact area corresponds to the future interconnection between the macropores of the bioceramic. In the present case, this line of contact remains discrete and has an estimated diameter of 100 $\mu$m.

A test temperature of 180° C. makes it possible, for short treatment times, to achieve significant bridging between the beads.

Figure 2:
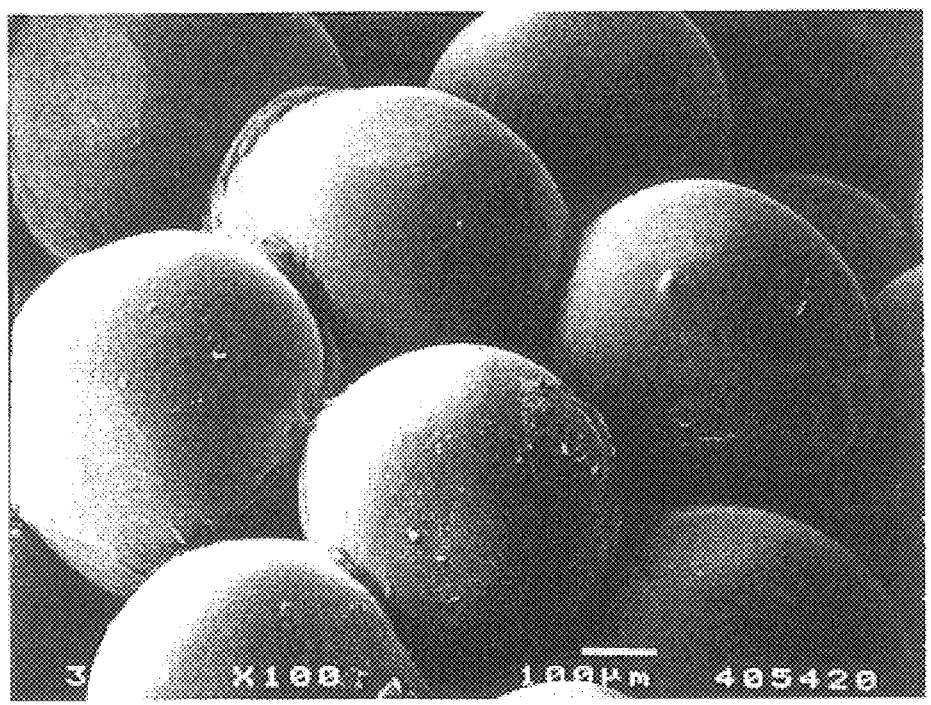
FIG. 2 is an electron microscope image of a monobloc structure formed from the interconnected particles.

The thermoformed PMMA particles thus form a monobloc structure having a certain number of spaces between the beads (see FIGS. 1 and 2).

Next, this monobloc structure is removed from the container and placed in a porous mold.

In the present embodiment, the mold is made of plaster.

It is also conceivable to use a mold made of ceramic, metal, resin or similar material.

The spaces between beads are then filed and impregnated with a dense suspension based on calcium phosphate in an aqueous medium.

This suspension, or slip, comprises hydroxyapatite (HA) or tricalcium phosphate ($\beta$ TCP), or else a mixture of them each up to the 100 % level.

The suspension, thus consisting of powder and water, will gradually dry around the monobloc structure because of capillary depression phenomena generated by the porosity of the plaster.

A "green" product—a two-phase mixture of ceramic and polymer beads—is therefore obtained.

In one particular embodiment of the invention, the mold has, in its walls, a reservoir containing a sufficient amount of slip.

This reservoir allows the monobloc structure to be continuously impregnated so that all the spaces are filled perfectly, this being so until the slip has dried. This reservoir is used in combination with the casting of the slip.

During casting of the suspension, a deflocation step is carried out in order to achieve optimum deagglomeration of the suspension.

A calcium phosphate suspension, for example a hydroxyapatite suspension, is defloculated by a polyelectrolyte of the carboxylate type, widely used in the ceramics industry; namely, ammonium polyacrylate (APa).

Under defined conditions (0.6% of APa and a pH of 11), various suspensions were tested using increasing HA contents, i.e. 82%, 84% and 86%.

The viscosities of these slips were then determined at a velocity gradient of 100 s$^{-1}$.

The results show that a suspension of 82% solids has a relatively low viscosity which allows the interstices between the PMMA spheres to be completely filled.

It should be understood that suspensions with a lower concentration of solids may be used, especially in order to reduce the viscosity and make it easier to impregnate the polymeric structure.

The "green" product obtained is then demoulded.

Next, in order to generate porosity, the "green" product undergoes a heat treatment at low temperature, but above the thermal degradation temperature of the compound used (approximately 200° C. in the present case).

In the present embodiment, the temperature of this treatment is below approximately 300° C.

This heat treatment will therefore make it possible to remove the beads, by burning off all the organic matter, and therefore to generate voids in their place.

Finally, in order to increase the cohesion and the rigidity of the product, the latter undergoes a sintering heat treatment at a temperature between 1100° C. and 1300° C.

A macroporous ceramic with controlled interconnections is thus obtained, this possibly being intended for bone replacement.

Figure 3:
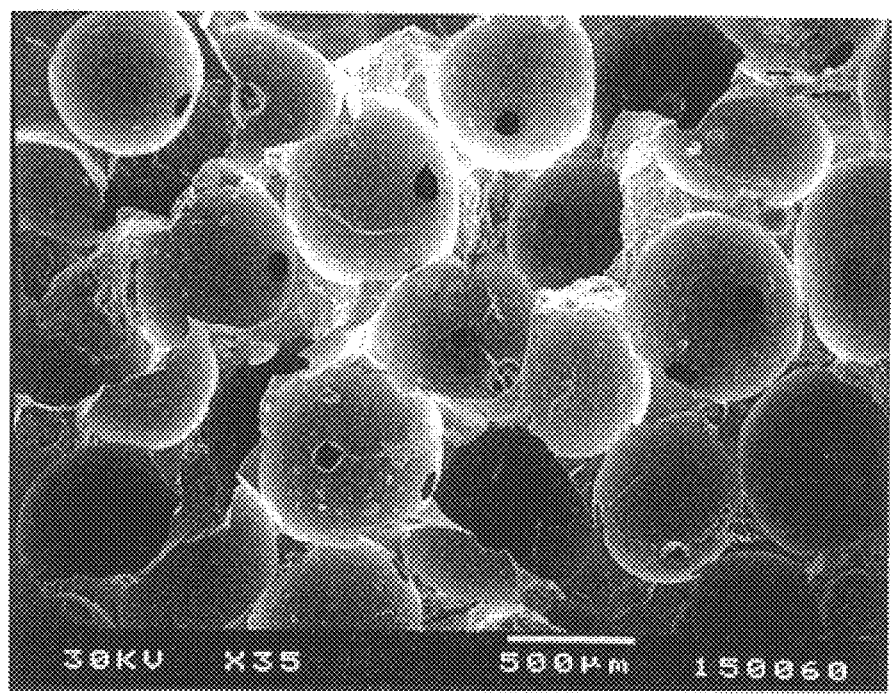
FIGS. 3 and 4 are electron microscope images of ceramics containing 500 μm pores, the interconnection diameters of which are 100 μm and 200 μm, respectively.
Figure 4:
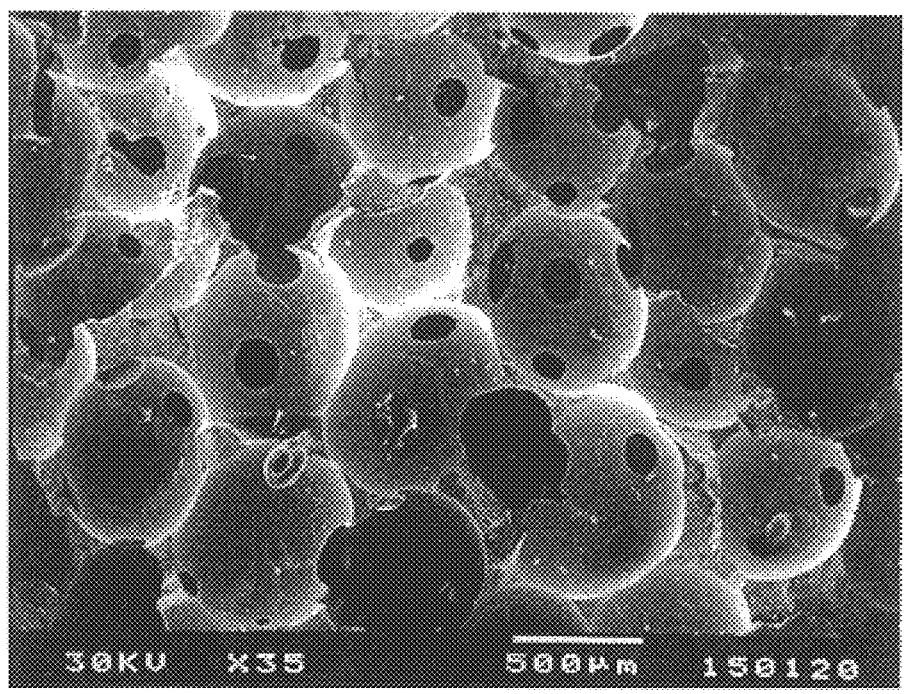

FIGS. 3 and 4 clearly indicate the control and the growth of the interconnection diameter (small black holes) for a 500 $\mu$m porosity.

It should be understood that the plaster mold can have various shapes, whether simple or complex.

Thus, it may have, for example, an approximately parallelepipedal or cylindrical shape, these being simple shapes.

Furthermore, walls of various shapes may be provided inside such a mold so as to obtain a ceramic of complex shape.

It should be understood, in fact, that the shape of the plaster mold determines that of the ceramic to be produced.

FIGS. 6a to 9c show examples of complex configurations of the ceramic obtained, and therefore of the mold.

Thus, it is possible to provide dense parts allowing mechanical reinforcement of certain regions of the replacement.

The polymeric edifice therefore does not include beads at the place where it is desired to have the dense part (s).

Figure 6A:
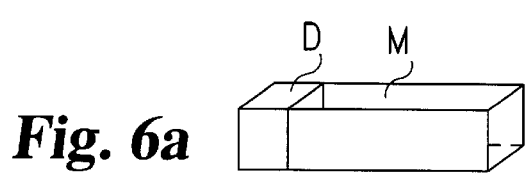
FIGS. 6a to 6c are diagrammatic perspective views of embodiments of bone replacements with a peripheral mechanical reinforcement.
Figure 6B:
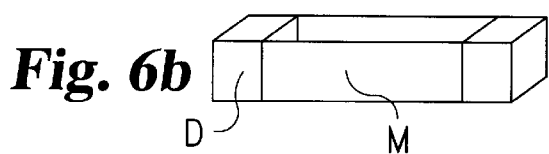
Figure 6C:
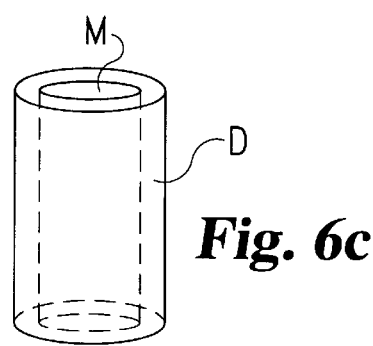

In FIGS. 6a to 6c, the densest parts D are located on the periphery of the replacement, whether this be parallelepipedal (FIGS. 6a and 6b) or cylindrical (FIG. 6c).

Dense parts inserted between macroporous parts may also be envisaged (not shown).

Figure 7A:
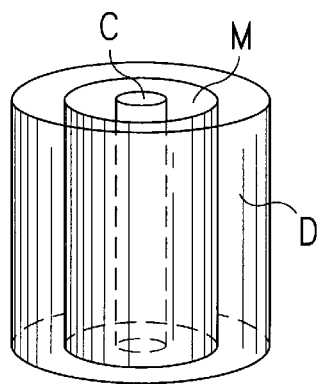
FIGS. 7a and 7b are diagrammatic perspective views of embodiments of bone replacements with a tubular mechanical reinforcement.
Figure 7B:
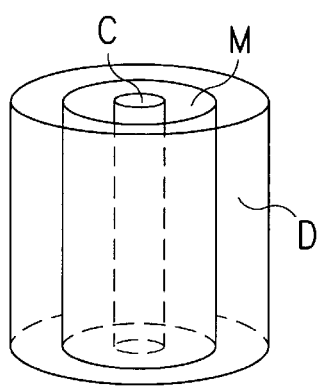

Furthermore, FIGS. 7a and 7b show an embodiment of a cylindrical replacement comprising a dense part D, a macroporous part M and a hollow part C.

In FIG. 7a, the dense part D is inserted between the hollow part C and the macroporous part M, while in FIG. 7b the dense part lies around the periphery of the replacement.

Figure 8A:
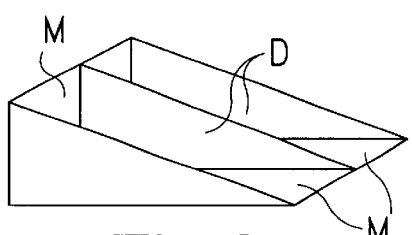
FIG. 8a to 8d are diagrammatic perspective views of bone replacements showing possible applications, especially for a tibial osteotomy of addition (FIGS. 8a to 8c).
Figure 8B:
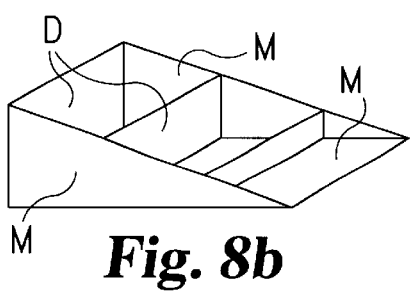
Figure 8C:
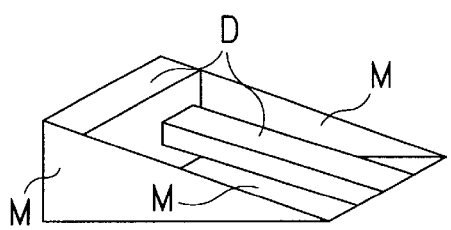
Figure 8D:
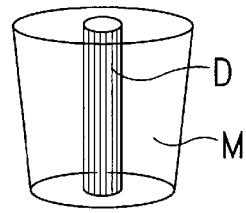
Figure 9A:
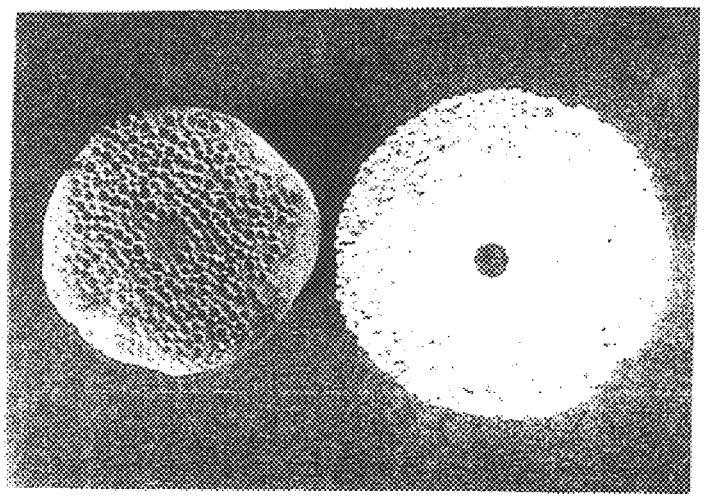
FIGS. 9a to 9c are optical micrographs illustrating the replacement of FIG. 8d, seen from above, from the side and in longitudinal section, respectively. In one particular embodiment, the macroporous ceramic is prepared from acrylic resin particles, such as polymethyl methacrylate (PMMA) particles, packed into a container.
Figure 9B:
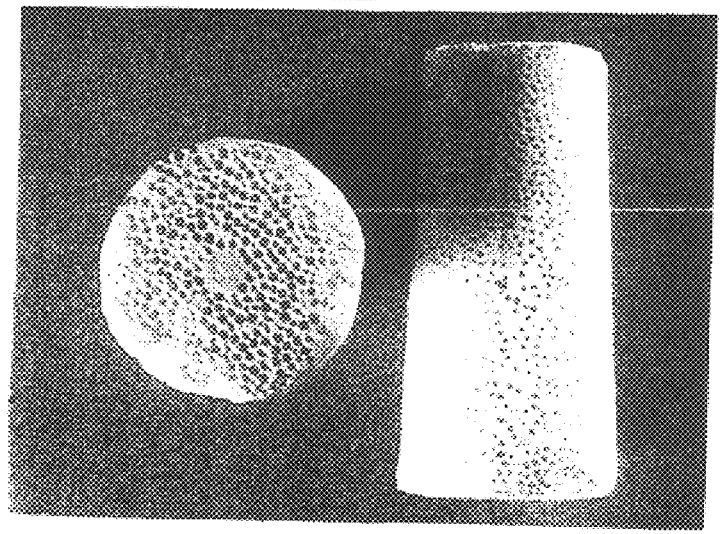
Figure 9C:
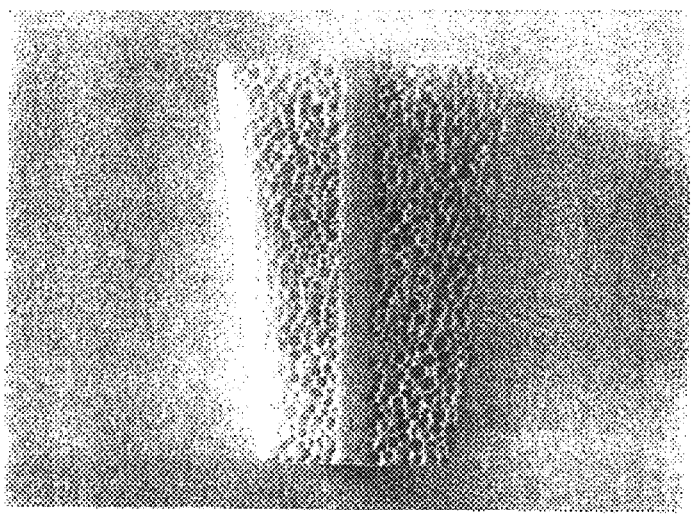

Finally, FIGS. 8a to 8c show replacements of complex shape, called "wedge"-shaped replacements, in which the dense or microporous parts are depicted at D and the macroporous parts at M.

In these embodiments, the parts M are inserted between the parts D.

Such replacements can, for example, be used in the case of tibial osteotomy of addition.

FIG. 8d and FIGS. 9a to 9c illustrate a replacement of frustoconical general shape, comprising an internal dense part D of cylindrical general shape and an approximately frustoconical external porous part.

The dense parts D are obtained, for example, by generating lower porosity, for example by using small-sized particles.

The strength of the replacement—and therefore its density—may also be increased by increasing the spaces between the particles so as to increase the amount of slip impregnated, or by removing the particles from certain regions and by filling these regions with slip.

Of course, the invention is not limited to the embodiments that have just been described In fact, it is possible to envisage other ceramic shapes, and therefore other mold shapes, or other particle shapes.

What is claimed is:

1. A process for preparing a macroporous synthetic ceramic said process comprising:

introducing particles of a pore-forming organic compound into a container;

thermoforming said particles at a temperature above the glass transition temperature of the pore-forming organic compound to provide a monobloc structure having coalescent particles;

contacting the monobloc structure with a calcium phosphate based suspension;

causing a liquid to diffuse from the monobloc structure;

removing the pore-forming organic compound to form a ceramic material having pores; and sintering the ceramic material at a temperature sufficient to provide the macroporous synthetic ceramic.

2. The process according to claim 1, wherein said thermoforming consists of homogeneously heating the pore-forming organic compound at a temperature above the glass transition temperature of the organic compound.

3. The process according to claim 2, wherein the pore-forming organic compound includes a thermoplastic polymer.

4. The process according to claim 3, wherein the pore-forming organic compound has an at least partially amorphous structure.

5. The process according to claim 1 wherein said thermoforming comprises:

preheating the container, at a temperature above the glass transition temperature of the pore-forming organic compound;

introducing the particles into the container;

welding the particles until the end of cooling;

cooling the particles to room temperature.

6. The process according to claim 1, wherein the pore-forming organic compound is selected from polymethyl methacrylate polymethacrylate, polystyrene, polyethylene and mixtures thereof.

7. The process according to claim 1, wherein said introducing includes introducing particles having a substantially spherical shape into the container.

8. The process according to claim 1, wherein said suspension comprises hydroxyapatite or tricalcium phosphate (β TCP), or a mixture thereof.

9. The process according to claim 1, wherein said removing includes heating to a temperature greater than or equal to the thermal degradation temperature of the pore-forming organic compound.

10. The process according to claim 1, wherein said removing includes heating to a temperature of about 1000° C. to about 1300° C.

11. The process according to claim 1 wherein the container is formed of a metallic, ceramic or polymeric material able to withstand at least the thermal degradation temperature of the pore-forming organic compound.

12. The process according to claim 1, wherein said monobloc structure is introduced into a porous mold having a predetermined shape.

13. The process according to claim 1, wherein said porous mold is selected from molds formed of material selected from plaster, ceramic, metal and resin.

14. The process according to claim 1, wherein said microporous synthetic ceramic has a pore diameter of between about 100 $\mu$m and 800 $\mu$m with interconnections of from between about 0.1 and about 0.8 times said diameter.

15. A synthetic ceramic obtained by the process according to claim 1, and wherein said synthetic ceramic comprises a plurality of micropores having a diameter of between about 100 $\mu$g and about 800 $\mu$m and wherein said plurality of micropores have interconnections between about 0.1 and about 0.8 times said diameter.

16. The synthetic ceramic according to claim 15, provided with a macrostructure having a porosity gradient.

* * * * *